US008852512B2

(12) United States Patent
Lam et al.

(10) Patent No.: US 8,852,512 B2
(45) Date of Patent: Oct. 7, 2014

(54) MONITOR AND A METHOD FOR MEASURING OXYGEN CONCENTRATION

(75) Inventors: Joseph K-W Lam, Bristol (GB); David Osborne, Bristol (GB); Norman Mark Ratcliffe, Bristol (GB)

(73) Assignee: Airbus Operations Ltd, Bristol (GB)

( * ) Notice: Subject to any disclaimer, the term of this patent is extended or adjusted under 35 U.S.C. 154(b) by 849 days.

(21) Appl. No.: 12/502,244

(22) Filed: Jul. 14, 2009

(65) Prior Publication Data

US 2010/0018119 A1 Jan. 28, 2010

(30) Foreign Application Priority Data

Jul. 28, 2008 (GB) .................................. 0813715.0

(51) Int. Cl.
*G01N 33/00* (2006.01)
*G01N 21/64* (2006.01)

(52) U.S. Cl.
CPC ...... *G01N 21/643* (2013.01); *G01N 2021/6439* (2013.01); *Y02T 10/34* (2013.01); *G01N 2021/6432* (2013.01); *F01M 21/12* (2013.01)
USPC .................... 422/82.08; 422/68.1; 422/400

(58) Field of Classification Search
USPC ...................... 422/400, 68.1, 82.08
See application file for complete search history.

(56) References Cited

U.S. PATENT DOCUMENTS

| 4,764,343 | A | 8/1988 | Nyberg |
| 5,030,420 | A * | 7/1991 | Bacon et al. ............... 422/82.07 |
| 5,043,285 | A | 8/1991 | Surgi |
| 5,919,710 | A | 7/1999 | Gord et al. |
| 6,251,342 | B1 | 6/2001 | Narula et al. |
| 6,531,097 | B1 * | 3/2003 | Vojnovic et al. ........... 422/82.07 |
| 7,356,464 | B2 | 4/2008 | Stella et al. |
| 7,456,969 | B2 | 11/2008 | Chabanis et al. |
| 2004/0062683 | A1 * | 4/2004 | Yam et al. ...................... 422/58 |
| 2006/0060788 | A1 | 3/2006 | Uchida et al. |
| 2006/0171845 | A1 | 8/2006 | Martin et al. |
| 2007/0070356 | A1 * | 3/2007 | Tan et al. ...................... 356/477 |
| 2007/0122311 | A1 | 5/2007 | Shahriari |

FOREIGN PATENT DOCUMENTS

| GB | 2132348 A | 7/1984 |
| WO | 9212424 A1 | 7/1992 |
| WO | 00/42418 A1 | 7/2000 |
| WO | 03/046422 A1 | 6/2003 |
| WO | 03046422 A1 | 6/2003 |
| WO | 2004044547 A3 | 5/2004 |

OTHER PUBLICATIONS

Xavier et al. Oxygen Sensing in Nonaqueous Media Using Porous Glass with Covalently Bound Luminescent Ru(II) Complexes Analytical Chemistry, vol. 70, No. 24, pp. 5184-5189 Dec. 15, 1998.*
UK Search Report for GB0813715.0 dated Nov. 5, 2008.

* cited by examiner

*Primary Examiner* — Sam P Siefke
(74) *Attorney, Agent, or Firm* — Lowe Hauptman & Ham, LLP

(57) ABSTRACT

A monitor for monitoring the concentration of oxygen in a fuel or in an ullage over a fuel comprises (i) a sensing element comprising a luminescent substance comprising a luminophore and a support in which the luminophore is covalently bound to the support, (ii) a light source arranged to irradiate the sensing element with light, and (iii) a photosensor arranged to detect light emitted from the luminescent substance. The luminescent substance may be, for example, a platinum porphyrin covalently bound to silica.

12 Claims, No Drawings

MONITOR AND A METHOD FOR MEASURING OXYGEN CONCENTRATION

RELATED APPLICATIONS

The present application is based on, and claims priority from, British Application Number 0813715.0, filed Jul. 28, 2008, the disclosure of which is hereby incorporated by reference herein in its entirety.

FIELD OF THE INVENTION

This invention relates to a monitor and method for the monitoring of the concentration of oxygen in a fuel or in an ullage over a fuel. More particularly, although not exclusively, the monitor and method of the invention may find specific application in measuring the concentration of oxygen in or above aviation fuel, for example, in the fuel tank of an aircraft or in a fuel supply tanker.

BACKGROUND ART

Aircraft fuel naturally contains some dissolved gas, typically air, and therefore typically contains some dissolved oxygen. The amount of oxygen in fuel decreases with pressure. Therefore, at cruising altitude (i.e., at low ambient pressure), oxygen is degassed from the fuel. From a safety standpoint, it is desirable to have fuel or fuel-rich environments contained in an inert atmosphere. Thus, the release of oxygen from fuel in such an environment is highly undesirable.

Also, evolved gas from the fuel may increase the risk of air pockets forming in the fuel system of the aircraft. Some aircraft fuel tank arrangements use gravity feed systems including siphons to transfer fuel within the fuel system. Air pockets present in the fuel tank system may act to disrupt the siphon effect in gravity feed systems, the pressure head possibly being insufficient to push the air down the pipes.

One known technology for estimating oxygen concentration uses electrochemical detection. However, most commonly used electrolytes are not suitable for extreme operating temperatures. In particular, they are not suitable for the low temperatures encountered in aviation applications.

More recently, oxygen monitors for aircraft fuel tanks have been developed in which the oxygen concentration is monitored by means of a probe containing a luminescent substance. Oxygen acts to quench the luminescence of the luminescent substance and therefore the concentration of oxygen can been derived from measurements of the light emitted from the luminescent substance.

WO 03/046422 describes one such system in which the oxygen concentration in an aircraft fuel tank is monitored by means of a monitor containing a fluorescent ruthenium complex.

US 2006/0171845A1 discloses the use of platinum (II) tetrakis(pentafluorophenyl)porphyrin as a fluorescent compound held within an amorphous fluorinated polymer matrix for the detection of oxygen in an aircraft fuel tank.

In order to be suitable for use in an aircraft fuel tank a monitor must be capable of withstanding the low temperatures, for example, −20° C. to which the fuel tanks are exposed when the aircraft is in flight. Furthermore, for obvious reasons it is desirable that the monitor be reliable and have a lifetime which is numbered in years rather than months. Furthermore, the materials used in the monitor must be compatible with aviation fuel.

The present inventors have found that the luminescence of some substances is effectively switched off by contact with the aviation fuel and therefore the sensing mechanism becomes inoperative. The reason for that is not known but it is possible that aviation fuel contains certain additives which act to prevent the luminescence. Furthermore, luminescent materials held in a polymer matrix can over time leach out from the polymer into the aviation fuel, thereby reducing the effectiveness of the monitor.

DISCLOSURE OF THE INVENTION

In order to mitigate at least some of the above mentioned problems the present invention provides a monitor for monitoring the concentration of oxygen in a fuel or in an ullage over a fuel comprising:

a sensing element comprising a luminescent substance comprising a luminophore and a support in which the luminophore is covalently bound to the support;

a light source arranged to irradiate the sensing element with light; and a photosensor arranged to detect light emitted from the luminescent substance.

The present inventors have found that covalently bonding the luminophore to a support effectively anchors the luminophore to the support and therefore inhibits leaching of the luminophore away from the sensing element and into the fuel. Surprisingly, the inventors have also found that covalently binding a luminophore to a support can counteract the inactivation of the luminophore by jet fuel, thereby allowing it to retain luminescent activity when used in contact with fuel.

In a particularly desirable embodiment, the monitor is suitable for use in an aircraft fuel tank. In a further embodiment the monitor is suitable for use in a ground based aviation fuel supply vehicle such as a fuel tanker or in an aviation fuel storage facility.

In a second aspect the invention provides an aircraft including a fuel tank provided with a monitor according to a first aspect of the invention.

In a third aspect of the invention, the invention provides a method of detecting oxygen in a fuel or in ullage space above a fuel comprising the steps of:

irradiating with light a sensing element comprising a luminescent substance comprising a luminophore covalently bound to a support, thereby exciting luminescence in the luminescent substance; and detecting light emitted from the luminescent substance.

Embodiments of the invention can advantageously be used in fuel-flow control applications in aviation to provide a fast and accurate means of monitoring the dissolved oxygen concentration in fuel. With knowledge of dissolved oxygen concentration in fuel, the risk of air pockets in pipes under gravity feed conditions may be gauged and appropriate action taken.

The term 'luminescent substance' as used herein is to be understood as referring to a substance which is useful in the detection of oxygen in accordance with the invention by means of luminescence and luminescence quenching. Luminescence can be considered to be an emission of light which does not result from the temperature of the luminescent substance but rather from the excitation of the luminescent substance, for example, by incident light. Luminescent quenching is the reduction of luminescence which results from the presence of a particular substance such as oxygen. Contact with a quenching substance allows the excited luminescent substance to move from an excited state to a ground state without emitting light, resulting in a reduction in the intensity of the luminescence.

Light emitted by the luminescent substance must be distinguished from light which is reflected or scattered from the indicated substance.

The term 'light' as used herein includes visible, infrared and ultraviolet light.

Luminescence is generally sub-divided into two forms known as fluorescence and phosphorescence which are well understood by the skilled person. Most substances which are luminescent are either fluorescent or phosphorescent, but in some cases it is possible that luminescence occurs by a combination of the two mechanisms.

The term 'luminophore' refers to an atom or group of atoms within the luminescent substance which is responsible for the luminescent properties of the luminescent substance. The luminescent substance of the invention comprises a luminophore covalently bound to a support. The luminophore may be directly bonded by a single covalent bound to the support but preferably will be bound to the support via a bridging group as described in more detail below.

The term 'support' should be taken to refer to any solid or semi-solid material to which the luminophore can be covalently bonded and which is suitable for use in the monitor of the present invention.

Advantageously, the support is a high surface area material, for example, having a surface area of at least 50 $m^2/g$, preferably at least 100 $m^2/g$ and especially preferably at least 150 $m^2/g$. The support material may be a finely divided solid such as a powder. Optionally the support is selected from the group consisting of silica, alumina and clay. Silica is an especially preferred support material. In an alternative embodiment, the support may be a polymeric material. Optionally the polymeric material is cross-linked. The support may be, for example, polystyrene optionally cross-linked, for example, with divinylbenzyene. Poly(styrene-co-divinylbenzene) is commercially available in a number of different grades in the form of beads. Furthermore, a number of modified poly(styrene-co-divinylbenzenes) are available having amine substituents which may be conveniently used to form bridging groups with luminophore compounds. Modified silicas having amine groups attached to their surfaces are also commercially available.

The luminescent substance will typically be prepared by reacting a luminescent compound with a support material to arrive at a product in which a luminophore derived from the luminescent compound is covalently bonded to the support. The skilled person will be aware of a number of suitable luminophores and luminescent compounds for use in the invention. The luminophore may for example comprise a metal complexed with a macrocycle. In a preferred embodiment the luminophore is a metal porphyrin complex, for example a platinum porphyrin or a ruthenium porphyrin. Preferably, the luminophore is a platinum porphyrin complex and more preferably the luminophore is a fluorinated platinum porphyrin complex. An especially preferred luminophore is derived from the reaction of platinum (II) tetrakis(pentafluorophenyl)porphyrin with a support.

The luminophore desirably has a high quantum yield, that is, it efficiently converts incident radiation into emitted radiation of a different wavelength.

Preferably, the luminescent substance is a phosphorescent substance and the emitted radiation is phosphorescent radiation.

The luminophore is covalently bound to the support either by a direct covalent bond or by a bridging group containing a chain of covalent bonds between the support and the luminophore.

The bridging group may be any group which is suitable for covalently linking the support to the luminophore. Optionally the luminophore is covalently bound to the support via a bridging group comprising an amine, ether or thioether functional group. For example, the bridging group could be an alkyl amine, alkylether or an alkylthioether bridging group.

In one embodiment, the luminescent substance may be represented by the structural Formula (I);

Support-R-luminophore                    (I)

In which R is either a direct covalent bond or a bridging group.

Bridging group R in Formula (I) above is in one embodiment represented by the formula $-A-N(A_1)-$, $-A-O-$, $-A-$ or $-A-S-$ where each A is a hydrocarbyl group including from 1 to 50 carbon atoms where hydrocarbyl is defined as an aliphatic or aromatic group optionally comprising one or more heteroatoms, and $A_1$ is a hydrocarbyl group comprising from 1 to 20 carbon atoms.

Optionally, the bridging group comprises one or more amine groups.

The luminescent substance is in one embodiment prepared by reacting a luminescent compound (which is a precursor to the luminophore group) with a support material. For example, the luminescent substance may be prepared by reacting a luminescent compound with a silica modified to carry on its surface amine-containing groups. As a particular example, the present inventors have prepared luminescent substances by reacting platinum (II) tetrakis(pentafluorophenyl)porphyrin with silicas carrying alkylamino groups on their surfaces.

The term 'sensing element' as used herein relates to any element arranged to detect the presence of oxygen in accordance with the present invention. For example, the sensing element may be a window of transparent polymeric material in which the luminescent substance is embedded.

The sensing element should be able to withstand the conditions experienced in use of the monitor, for example, where the monitor is a monitor in aircraft fuel tank the luminophore should be capable of withstanding repeated low temperatures and contact with aviation fuel over a working life of at least one month and preferably at least one year.

The sensing element of the invention comprises the luminescent substance. In some cases the luminescent substance may be used alone in its unmodified form as the sensing element, for example, where the luminescent substance is such that it can be attached directly to the tip of an optical fibre and is suitable for direct contact with the fuel to be monitored. However, it will often be preferred to combine the luminescent substance with one or more other materials to form the sensing element. For example, the luminescent substance may be dispersed in one or more polymeric matrix materials. Such polymeric materials may improve the mouldability of the mixture allowing the sensing element to be manufactured in a particular desired form. The matrix material will be desirably be chemically unreactive towards the luminescent substance, be stable in the presence of a fuel, be sufficiently transparent to the light irradiated onto the luminescent substance from the light source and to the light emitted from the luminescent substance, and also be sufficiently permeable to oxygen to allow oxygen from the fuel to travel through the matrix material to the luminescent substance in a reasonable timescale.

Polysiloxanes are known to have good oxygen permeability and in one embodiment the matrix material comprises a polysiloxane. For example, the matrix material may be a mixture of polystyrene and polysiloxane. Preferably, the matrix material comprises at least 1%, more preferably at least 3% by weight of polysiloxane. A preferred matrix material is a mixture of polystyrene and polysiloxane in which the polysiloxane is present in the range of from 1 to 20%, preferably 1 to 10% by weight.

Optionally, the polymeric matrix material is a film forming material and the sensing element is in the form a film or coating. The film may be prepared by known techniques, for example, either from a melt of the polymer matrix material and the luminescent substance or a liquid dispersion comprising the matrix material and the luminescent substance which dries to form a film. Advantageously, the sensing element is a film comprising a polymeric matrix material and the luminescent substance dispersed in the polymeric matrix material, the film being associated with, for example, in contact with one or more optical elements such as an optical fibre through which the incident and emitted light right radiation can be carried.

In addition to the light source, the sensing element and the photosensor, the monitor of the invention optionally comprises one or more additional optical elements such as filters, reflectors and optical fibres for conveying light to and from the sensing element. Preferably, the monitor comprises an optical fibre carrying light from the light source to the sensing element and an optical fibre for carrying light from the sensing element to the photosensor. The optical fibre carrying light from the light source to the sensing element is optionally the same optical fibre which is used to carry from the sensing element to the photosensor, that is, a single optical fibre is used for both tasks. Preferably, the or each optical fibre is in direct contact with the sensing element.

Preferably, the sensing element is mounted in a vessel for storing the fuel, for example, a fuel tank and the light source and photosensor are located outside the vessel and communicate with the sensing element via optical elements such as optical fibres. That arrangement has the advantages that the monitor occupies a minimum of space inside the fuel tank and the electrical components of the light source and photosensor are safely located remote from the fuel tank.

The light source may be a light-emitting diode (LED). The light source may comprise one or more LEDs. The or each LED may be low-power LEDs. For example, the LEDs may be configured to be operated by means of electrical power of less than 500 mW and preferably less than 100 mW. The or each LED may for example be arranged to emit light having a maximum radiant intensity of less than 10 mW/Sr (Watts per Steradian) and possibly less than 1 W/Sr. The or each LED may be arranged to emit light having a maximum power density of less than 1 kilowatt per $cm^2$ and possibly less than 10 watts per $cm^2$. The light source when provided in the form of one or more LEDs may have the advantage of having a relatively long life span. For example, the estimated time to failure for the or each LED may exceed 10,000 hours of use. The average life time of the or each LED may therefore exceed several years, thereby requiring little or no maintenance. The light source may be a laser. The light emitted by the light source to excite the luminescent substance is optionally ultraviolet (UV) light. In an alternative embodiment, the exciting radiation is visible light.

The light source may comprise a filament light bulb. The light source may comprise a fluorescent tube. The light source may comprise one or more filters. The light source may be pulsed during operation of the monitor, such that the light source irradiates the substance with pulsed light. Alternatively, the light source is arranged to irradiate the substance with light of a substantially constant intensity during operation of the monitor.

The photomonitor may comprise a photodiode. The photomonitor may detect light in the visible spectrum. The monitor may comprise a filter arranged between the photomonitor and the sensing element. The filter may absorb substantially all light from the light source that is incident upon the filter. The filter may transmit light from the luminescent substance.

The monitor may be arranged to output a signal dependent on the intensity of light detected by the photomonitor. The monitor may be arranged to output a signal, which varies in inverse proportionality to changes in the electrical signal outputted directly by the photomonitor. The monitor may be arranged to output a signal, which is dependent on, for example proportional to, the concentration of oxygen in the fuel or ullage space as measured by the monitor. The output of the monitor may be derived from a measurement of the intensity of light as detected by the photomonitor at a time when the luminescent substance is being irradiated by the light source. Alternatively, or additionally, the output of the monitor may be derived, at least in part, from a measurement of the intensity of light as detected by the photomonitor at a time when the luminescent substance is not being irradiated by the light source.

Advantageously, the monitor is arranged to monitor the decay in intensity of light emitted from the luminescent substance following a pulse of incident radiation from a light source. By monitoring the rate of decay of emitted radiation rather than simply monitoring the intensity of emitted radiation at a given level of incident radiation the monitoring may be less subject to variations caused by aging of the sensing element.

The monitor of the invention may be used to give a single measurement of oxygen concentration. Alternatively, the monitor may be used to monitor the concentration of oxygen over a period of time or continuously.

The monitor of the invention may be used to monitor the concentration of oxygen in or above any fuel. Preferably, the fuel is a hydrocarbon-based fuel. The fuel may be a fuel derived from petroleum. In a preferred embodiment the fuel is a jet fuel. The fuel may comprise kerosene. The fuel may comprise a naphtha-kerosene. The fuel may, for example, be jet A, jet A-1, jet B, or TS-1 fuel. In a preferred embodiment the fuel is jet A fuel.

The fuel may be contained in any vessel such as a fuel tank or conduit such as fuel supply line. In a preferred embodiment, the monitor is located in a fuel tank and is in direct contact with the fuel in the fuel tank. In another preferred embodiment, the monitor is located in a fuel tank and is arranged to monitor the concentration of oxygen in an ullage space above the fuel.

In a further aspect the invention provides an aircraft including a fuel tank which is provided with a monitor according to the invention.

In a further aspect the invention provides a fuel handling apparatus which is provided with a monitor according to the invention. The fuel handling facility may be, for example, a fuel storage depot or a fuel tanker vehicle.

In a further aspect of the invention the invention provides a method of controlling the oxygen concentration in a fuel comprising the steps of:

providing a sensing element comprising a luminescent substance comprising a luminophore covalently bound to a support in contact with the fuel or in an ullage space above the fuel;

irradiating with light the sensing element thereby exciting luminescence is a luminescent substance;

detecting light emitted from the luminescent substance;
estimating the oxygen concentration in the fuel or the ullage space based on the detected light; and
treating the fuel with a diluent gas in dependence upon the estimated level of oxygen concentration.

The diluent gas may be nitrogen enriched air.

DETAILED DESCRIPTION

Certain illustrative embodiments of the invention will now be described in detail by way of example only.

EXAMPLE 1

Photoluminescent Compounds Prepared from Silica as Support and Platinum (II) Tetrakis(Pentaflurophenyl)Porphyrin as Luminophore Precursor.

Four different functionalized silicas were used:
Aminopropyl functionalized silica;
2-(4-ethylenediaminobenzyl)ethyl functionalized silica;
3-(diethylenetriamino)propyl functionalized silica; and
3-propylethylenediamine functionalized silica.

The functionalised silicas were obtained from Fisher-Acros and typically 9% of the silanol (SiOH) groups were functionalised.

The structure of the functionalized silicas used can be regarded as, (idealized):

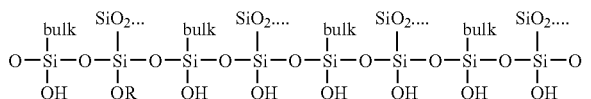

where R=
—$CH_2$—$CH_2$—$CH_2$—$NH_2$ (aminopropyl, AP)
—$CH_2$—$CH_2$—$CH_2$—NH—$CH_2$—$CH_2$—$NH_2$ (3-(ethylenediamino)propyl, PED)
—$CH_2$—$CH_2$—$CH_2$—NH—$CH_2$—$CH_2$—NH—$CH_2$—$CH_2$—$NH_2$ (3-(diethylenetriamino)propyl, DETAP)
—$CH_2$—$CH_2$—$C_6H_4$—NH—$CH_2$—$CH_2$—$NH_2$ (2-(4-ethylenediaminobenzyl)ethyl, EDABE)

Platinum (II) tetrakis(pentaflurophenyl)porphrin has the structure:

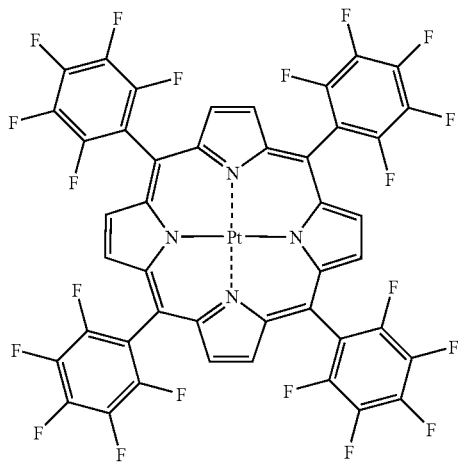

Without wishing to be bound by theory, the porphyrin is believed to undergo substitution of the para fluorine on one of the pentafluorophenyl groups, reacting with an $NH_2$ or NH group on the functionalised silica. (In the case of the silicas with more than one amino group, it has not yet been established which amino group has reacted). A molecule of HF is eliminated and the overall structure of the silica/porphyrin adduct, for example, the aminopropyl adduct, might thus be represented as:
Bulk silica-Si—O—$CH_2$—$CH_2$—$CH_2$—NH-porphyrin
with the porphyrin being covalently bound to the silica through the aminopropyl bridging group.

And so in general, one possible structure for the luminescent compound is:
Silica-R-porphyrin, where R is a bridging group comprising an amino group.

Platinum (II) tetrakis(pentafluorophenyl)porphyrin (20 mg) and functionalized silica (500 mg), were stirred in diglyme (15 ml) at 140° C. for 6 hours, in anhydrous conditions. The solid product was obtained by filtration under reduced pressure, washed with toluene (4×5 ml) and dried at 50° C. for 12 hours.

Similar preparations were carried out at the increased temperature of 160° C., and it was found that the gains in terms of reaction rate were not significant. However, by increasing the initial mass of dye to 100 mg (instead of 20 mg), the yields were significantly increased.

EXAMPLE 2

Luminescent Substances Prepared from Aminofunctionalised Polystyrene as Support and Platinum (II) Tetrakis(Pentafluorophenyl)Porphyrin as Luminophore Precursor.

Platinum (II) tetrakis(pentafluorophenyl)porphyrin (20 mg) and amino functionalized poly(styrene-co-divinylbenzene) (100 mg), were stirred in diglyme (15 ml) at 140° C. for 6 hours, in anhydrous conditions. The solid product was obtained by filtration under reduced pressure, washed with toluene (4×5 ml) and dried at 50° C. for 12 hours.

EXAMPLE 3

Polymer Films Comprising Porphyrin/Silica Adducts.

The porphyrin/silica adducts prepared in Example 1 were incorporated into polymer films, according to the following method. The polystyrene used was ex. BDH, and had a molecular weight of approximately 100,000. The polysiloxane was in the form of a conformal coating from Dow Corning comprising 64% octamethyltrisiloxane, 30% mixture of dimethylsiloxane, methylmethoxysilane, phenylmethoxysilane, methyl silsesqioxane and phenyl silsesquioxane, 3% toluene and 1.7% trimethoxy(methyl)silane.

Toluene (5 g) was stirred with polystyrene (500 mg) and conformal coating (20 mg) until the polystyrene had dissolved. The porphyrin/silica adduct (20 mg) was added and dispersed by stirring. Films were cast on glass sides, allowing the toluene to evaporate on standing. A range of samples was prepared which contained various proportions of conformal coating and polystyrene. The polysiloxane content was kept greater than 3% by weight in order to retain air permeability.

Monitor Measurements

The porphyrin/silica adducts prepared in Example 1 were tested in both air and jet fuel A for oxygen sensing ability. The oxygen concentration was varied either by the use of vacuum or by flooding with nitrogen. In the latter case nitrogen was blown over the adduct dry or bubbled through jet fuel containing the adduct. The adducts were irradiated, at 400 nm, by either uv LEDs or a uv lamp. Changes in phosphorescence were noted (by visual inspection) for all of the samples. Photodiodes were used to measure emitted light.

All of the porphyrin/silica adducts displayed a rapid response to the presence of oxygen, which quenched the phosphorescence. Similar results were obtained with the samples in which the porphyrin/silica adduct was dispersed in a polystyrene/polysiloxane matrix.

Ageing Studies

The porphyrin/silica adducts were heated according to the following method in a range organic solvents, including jet fuel, to simulate ageing over a long period of time.

The porphyrin/silica adduct (120 mg) was stirred in toluene (10 ml) at 45° C. for 1 hour, to remove any traces of unbonded porphyrin. UV spectroscopy of a sample of the solvent then revealed no trace of dye. After filtering this was repeated using fresh solvent, heating and stirring for another 3 hours. Further UV measurements revealed no trace of porphyrin in the solvent. After stirring for 4 days at room temperature, more UV readings were taken, with no evidence of porphyrin dissolved in the dye.

This procedure was repeated with jet fuel, with the same results as for toluene. Filtered samples of the adducts revealed that they still functioned as oxygen sensors after these treatments. XPS studies have confirmed that the porphyrin is bonded to the silica.

The results show that the porphyrin remained bonded to the silica, and oxygen sensing ability was preserved.

The invention claimed is:

1. A monitor for monitoring the concentration of oxygen in a fuel or in an ullage over a fuel, comprising:
    a sensing element comprising a luminescent substance comprising a luminophore and a support in which the luminophore is covalently bound to the support by a bridging group, and wherein the support is a high surface area material having a surface area equal to or greater than 50 $m^2$ per gram of the support;
    in which the sensing element further comprises a polymeric matrix material surrounding the luminescent substance, wherein the polymeric matrix material comprises a polysiloxane;
    a light source arranged to irradiate the sensing element with light; and
    a photosensor arranged to detect light emitted from the luminescent substance.

2. A monitor as claimed in claim 1 in which the luminophore is derived from a metal porphyrin complex.

3. A monitor as claimed in claim 2 in which the metal porphyrin complex is platinum (II) tetrakis (pentafluorophenyl) porphyrin.

4. A monitor as claimed in claim 1 in which the support is silica.

5. A monitor as claimed in claim 1 in which the luminophore is covalently bound to the support via an amine, ether, hydrocarbyl or thioether bridging group.

6. A monitor as claimed in claim 1 which comprises an optical fibre for carrying light from the light source to the sensing element an optical fibre for carrying light from the sensing element to the photosensor.

7. An aircraft including a fuel tank which is provided with a monitor as claimed in claim 1.

8. An aircraft as claimed in claim 7 in which the monitor is positioned to measure the oxygen concentration in the fuel in the fuel tank.

9. An aircraft as claimed in claim 7 in which the monitor is positioned to measure the oxygen concentration in the ullage above the fuel in the fuel tank.

10. A fuel handling facility which is provided with a monitor as claimed in claim 1.

11. A method of detecting oxygen in a fuel or in an ullage space above the fuel, comprising:
    irradiating with light a sensing element comprising a luminescent substance comprising a luminophore and a support in which the luminophore is covalently bound to the support by a bridging group, and wherein the support is a high surface area material having a surface area equal to or greater than 50 $m^2$ per gram of the support; in which the sensing element further comprises a polymeric matrix material surrounding the luminescent substance, wherein the polymeric matrix material comprises a polysiloxane, thereby exciting luminescence in the luminescent substance; and
    detecting light emitted from the luminescent substance.

12. A method of controlling oxygen concentration in a fuel or in an ullage space above the fuel, comprising:
    providing a sensing element comprising a luminescent substance comprising a luminophore and a support in which the luminophore is covalently bound to the support by a bridging group, and wherein the support is a high surface area material having a surface area equal to or greater than 50 $m^2$ per gram of the support; in which the sensing element further comprises a polymeric matrix material surrounding the luminescent substance, wherein the polymeric matrix material comprises a polysiloxane, the sensing element being in contact with the fuel or in the ullage space above the fuel;
    irradiating with light the sensing element thereby exciting luminescence in the luminescent substance;
    detecting light emitted from the luminescent substance;
    estimating the oxygen concentration in the fuel or the ullage space based on the detected light; and
    treating the fuel with a diluent gas in dependence upon the estimated level of oxygen concentration.

* * * * *